(12) United States Patent
von Geldern et al.

(10) Patent No.: US 10,329,279 B2
(45) Date of Patent: *Jun. 25, 2019

(54) CHIRAL SYNTHESIS METHOD FOR PRODUCING CIS-IMIDAZOLINE COMPOUNDS FOR PHARMACEUTICAL USE

(71) Applicant: Unity Biotechnology, Inc., Brisbane, CA (US)

(72) Inventors: Thomas W. von Geldern, Richmond, IL (US); Bradley Backes, San Francisco, CA (US); Bing Chen, Shanghai (CN)

(73) Assignee: Unity Biotechnology, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/955,474

(22) Filed: Apr. 17, 2018

(65) Prior Publication Data

US 2018/0362510 A1    Dec. 20, 2018

Related U.S. Application Data

(63) Continuation of application No. 15/693,061, filed on Aug. 31, 2017, now Pat. No. 9,988,368, which is a continuation of application No. PCT/CN2017/088787, filed on Jun. 16, 2017.

(51) Int. Cl.
    *C07D 403/06* (2006.01)
    *C07D 233/54* (2006.01)
    *C07D 233/64* (2006.01)

(52) U.S. Cl.
    CPC ......... *C07D 403/06* (2013.01); *C07D 233/54* (2013.01); *C07D 233/64* (2013.01)

(58) Field of Classification Search
    CPC ... C07D 233/54; C07D 233/64; C07D 403/06
    USPC ....................................................... 544/370
    See application file for complete search history.

(56) References Cited

U.S. PATENT DOCUMENTS

| 6,617,346 | B1 | 9/2003 | Kong et al. |
| 6,734,302 | B2 | 5/2004 | Kong et al. |
| 7,705,007 | B2 | 4/2010 | Fotouhi et al. |
| 9,849,128 | B2 | 12/2017 | Laberge et al. |
| 9,855,266 | B2 | 1/2018 | Laberge et al. |
| 9,988,368 | B1* | 6/2018 | von Geldern ........ C07D 403/06 |
| 2005/0282803 | A1 | 12/2005 | Haley et al. |
| 2007/0129416 | A1 | 6/2007 | Ding et al. |
| 2012/0088915 | A1 | 4/2012 | Johnston et al. |
| 2013/0225603 | A1 | 8/2013 | Chavala et al. |
| 2016/0339019 | A1 | 11/2016 | Laberge et al. |
| 2017/0196858 | A1 | 7/2017 | Laberge et al. |
| 2017/0198253 | A1 | 7/2017 | Laberge et al. |
| 2017/0216286 | A1 | 8/2017 | Kirkland et al. |
| 2017/0348307 | A1 | 12/2017 | Laberge et al. |

FOREIGN PATENT DOCUMENTS

| CN | 103923067 B | 8/2016 |
| WO | WO-2007082805 A1 | 7/2007 |
| WO | WO-2015116740 A1 | 8/2015 |

OTHER PUBLICATIONS

Davis, Tyler A. et al. Catalytic, enantioselective synthesis of stilbene cis-diamines: A concise preparation of (-)-Nutlin-3 a potent p53/MDM2 inhibitor. Chem. Sci. 2:1076-1079 (2011).
International Application No. PCT/CN2017/088787 International Search Report and Written Opinion dated Mar. 23, 2018.
Miyazaki, et al. Lead optimization of novel p53-MDM2 interaction inhibitors possessing dihydroimidazothiazole scaffold. Bioorg Med Chem Lett. Feb. 1, 2013;23(3):728-32.
U.S. Appl. No. 15/693,061 Pre-Interview Communication dated Jan. 25, 2018.
Yu, et al. Design, synthesis and biological evaluation of sulfamide and triazole benzodiazepines as novel p53-MDM2 inhibitors. Int J Mol Sci. Sep. 5, 2014;15(9):15741-53.
Zheng, et al. Design, synthesis and in vitro and in vivo antitumour activity of 3-benzylideneindolin-2-one derivatives, a novel class of small-molecule inhibitors of the MDM2-p53 interaction. Eur J Med Chem. Jun. 23, 2014;81:277-88.

\* cited by examiner

*Primary Examiner* — Deepak R Rao
(74) *Attorney, Agent, or Firm* — Michael Schiff; Wilson Sonsini Goodrich & Rosati

(57) ABSTRACT

This invention provides a method for enantioselective synthesis of cis-imidazolines and related structures through chiral resolution. A chiral acid is used to separate enantiomeric precursors of the cis-imidazolines from a racemic mixture by selective crystallization. Both enantiomers can be cyclized into the desired cis-imidazoline by complementary pathways. Compounds can be synthesized according to the invention with an enantiomeric excess as high as 99%. Cis-imidazolines such as Nutlin-3a prepared according to this invention may be used for treating cancer, killing senescent cells, or treating senescence-associated conditions.

18 Claims, 9 Drawing Sheets

When Compound I is (L)-mandelate conversion to cis-imidazolines with the biologically-active absolute stereochemistry is accomplished through the following scheme:

When Compound I is (L)-mandelate conversion to cis-imidazolines with the biologically-active absolute stereochemistry is accomplished through the following scheme:

When Compound II is (D)-mandelate conversion to cis-imidazolines with the biologically-active absolute stereochemistry is accomplished through the following scheme:

When Compound II is (D)-mandelate conversion to cis-imidazolines with the biologically-active absolute stereochemistry is accomplished through the following scheme:

CHIRAL SYNTHESIS METHOD FOR PRODUCING CIS-IMIDAZOLINE COMPOUNDS FOR PHARMACEUTICAL USE

CROSS-REFERENCE TO RELATED APPLICATION

This application is a continuation of U.S. patent application Ser. No. 15/693,061, filed Aug. 31, 2017, which is a continuation of PCT/CN2017/088787, filed Jun. 16, 2017, the contents of which are herein incorporated by reference in their entirety.

BACKGROUND

Certain cis-imidazolines are antagonists of MDM2 and MDMX. They have utility as cancer chemotherapeutics by triggering or restoring apoptosis in cells with defective or inactive p53 tumor suppressor protein. This is explained for example, in U.S. Pat. Nos. 6,734,302; 6,617,346; and 7,705,007 and pre-grant publications US 2005/0282803 A1; US 2007/0129416 A1; and US 2013/0225603 A1. Cis-imidazolines such as Nutlin-3a are also being developed for killing senescent cells and treating senescence-associated conditions: US 2016/0339019 A1

Miyazaki et al., Bioorganic & Medicinal Chemistry Letters 23 (2013) 728-732 discusses lead optimization of novel p53-MDM2 interaction inhibitors possessing a dihydroimidazothiazole scaffold. Yu et al., Int. J. Mol. Sci. 2014, 15, 15741-15753, discusses the design, synthesis and biological evaluation of sulfamide and triazole benzodiazepines. CN 103923067 B describes MDMX/MDM2 small molecule inhibitors, their preparation and use.

The biological activity of these cis-imidazolines typically resides in a single enantiomer. Several methods for the preparation of single-enantiomer versions of appropriately-substituted cis-imidazolines have been described. In WO2007/082805 and related patents, compounds are first prepared in racemic form, and then separated using chiral-HPLC strategies. US 2012/0088915 A1 describes an alternative approach in which a chiral catalyst is used to induce asymmetry into a key bond-forming step.

However, neither of these approaches is optimal for the large-scale preparation of chirally-pure cis-imidazolines of the type referred to above. Typical chiral HPLC-columns have a loading limit; to scale up a synthesis requires multiple purification runs, increasing the time required for synthesis, plus dramatically increasing the use of solvents and modifiers. The catalyst described in US 2012/0088915 A1 is itself prepared through a multi-step synthetic route; the overall synthesis of the final target requires a substantial number of additional chemical transformations.

SUMMARY OF THE INVENTION

This invention provides a method for enantioselective synthesis of cis-imidazolines and related structures through chiral resolution. A chiral acid is used to separate enantiomeric precursors of the cis-imidazolines from a racemic mixture by selective crystallization. Both enantiomers can be cyclized into the desired cis-imidazoline by complementary pathways. Compounds can be synthesized according to the invention with an enantiomeric excess as high as 99%. Cis-imidazolines prepared according to this invention may be used for treating cancer, killing senescent cells. or treating senescence-associated conditions. The described methods are readily scalable and suitable for the preparation of material in quantities sufficient for clinical development.

The invention includes methods for chemically synthesizing cis-imidazolines. A racemic mixture of a precursor according to Formula (A) can be combined with a chiral non-racemic aromatic acid according to Formula (B). A stereoisomer of the precursor that associates with the chiral acid to produce a minimally-soluble crystalline or amorphous salt under the reaction conditions is then separated from the other enantiomer, which may or may not also be associated with the chiral acid.

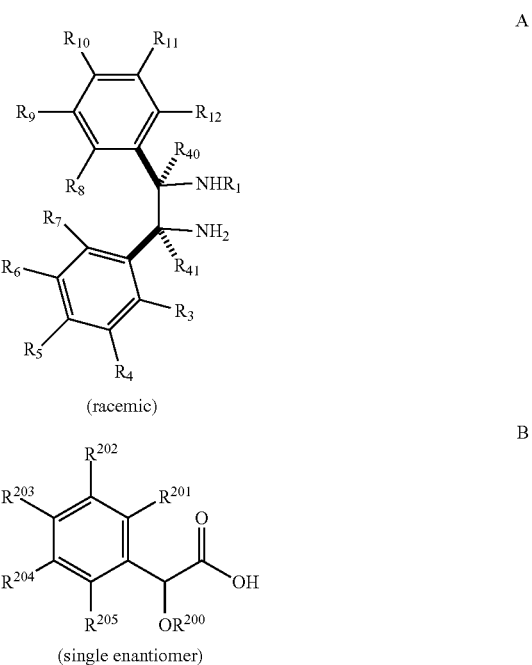

This is exemplified by:

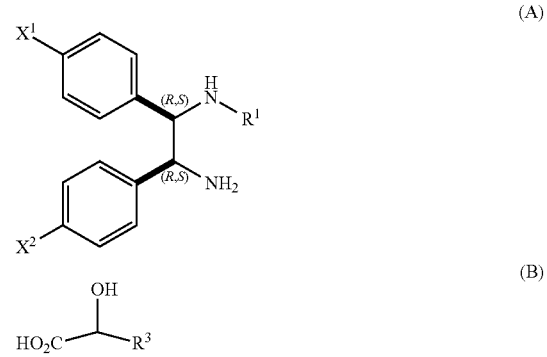

This invention takes advantage of a difference in physicochemical properties that result when one of the two enantiomers of A interact with the single enantiomer of B to form a diastereomeric salt. Any separation process that takes advantage of the difference may be used: for example, crystallization or salt formation under conditions where one enantiomer forms crystals or a salt, but the other does not.

After the reaction of A with B, the optically-enriched A can be converted to the free base by, for example, washing the salt with a basic solution, prior to further processing. In some cases, each enantiomer can be processed separately, and via a distinct sequence of chemical steps, to generate the same target cis-imidazoline. This approach is chemically efficient, since both enantiomers of A are converted to product.

Where the objective is to synthesize 4-[[(4S,5R)-4,5-bis (4-chlorophenyl)-4,5-dihydro-2-[4-methoxy-2-(1-methyl-ethoxy)phenyl]-1H-imidazol-1-yl]carbonyl]-2-piperazinone (Nutlin-3a), several distinct applications of this approach are possible. R' can be, for example tert-butyloxycarbonyl (BOC), benzyloxycarbonyl (Cbz), 9-fluorenylmethoxycarbonyl (Fmoc), allyloxycarbonyl (Alloc), or another amine protecting group. Alternatively, R' could be a fragment that will eventually be incorporated into the final product, for example

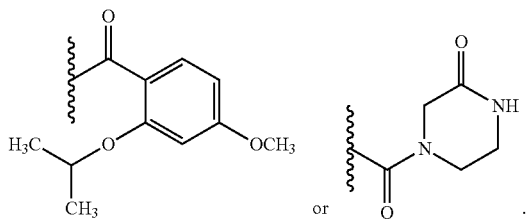 [SMILES: *C(=O)c1ccc(OC)cc1OC(C)C ; *C(=O)N1CCNC(=O)C1]

$R^3$ can be phenyl, $X^1$ and $X^2$ can be chloride, and the chiral acid (Formula B) can be D-mandelic acid or L-mandelic acid.

Subsequent synthetic steps typically include selective derivatization of the two nitrogen atoms of formula A, followed by a ring closing reaction to form an imidazoline ring. For example, to prepare Nutlin-3a, formula A is acylated on nitrogen (with a deprotection step if necessary) to provide Intermediate C, which is subsequently cyclized to give the final product.

INTERMEDIATE C

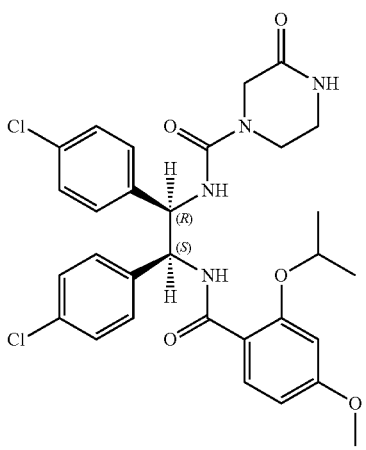

Cis-imidazolines prepared according to the synthetic methods of this invention may have a high degree of enantiomeric excess, as high as 90%, 99% or more. They may be tested for biological activity by combining with isolated cells (such as cancer or senescent cells) and determining the effect of the test compound on the cells.

Optionally, the synthesis can include using one or more reagents that include an isotopic label such as deuterium.

The resulting cis-imidazolidines can be used as internal standards for measuring the concentration of cis-imidazolidine, for example, in a biological sample taken from a subject or patient who is being administered the cis-imidazolidine as part of clinical care.

Cis-imidazolidines prepared according to the synthetic methods of this invention can be used, for example, to inhibit the MDM2 or MDMX receptor mediated pathway. The invention includes killing or inhibiting the growth of a cell (such as a cancer cell or a senescent cell) or a cell population with a cis-imidazolidine.

Cis-imidazolidines prepared according to the synthetic methods of this invention can be provided as a salt and/or combined with an excipient to yield a pharmaceutical composition suitable for human administration. Thus, the invention includes a pharmaceutical composition comprising a compound prepared according to any of the methods and a pharmaceutically compatible excipient. The invention includes a compound prepared according to any of the methods for use in medicine, or for the preparation of a medicament: for example, to treat cancer or a senescence-associated condition.

Other aspects of the invention will be apparent from the description that follows, the working examples, the appended claims, and the accompanying drawings.

DRAWINGS

FIGS. 1(A), 1(B), 1(C) and 1(D) are synthetic schemes to produce Nutlin-3a, an exemplary cis-imidazoline, according to the methods of this invention. Stereoisomers can be resolved with a chiral acid before or after derivitization of one of the amines of the intermediate.

FIGS. 2(A), 2(B), and 2(C) provide a detailed overview of the synthetic method for producing the cis-imidazoline Nutlin-3a. Once the stereoisomers are resolved, either isomer can be derivatized to produce the target compound through its own synthetic pathway.

FIG. 4 is a synthetic scheme used to produce a deuterated form of Nutlin-3a.

DETAILED DESCRIPTION

In view of the deficiencies of current methods of making cis-imidazolidines, there is a need for a short, chemically-efficient and scalable approach to the synthesis of cis-imidazolines like Nutlin-3a which can be used as antagonists of the MDM2 and MDMX mediated pathways. This disclosure provides an efficient and flexible approach to preparing key intermediates, and for converting these to cis-imidazolines final products.

Figure 1A:
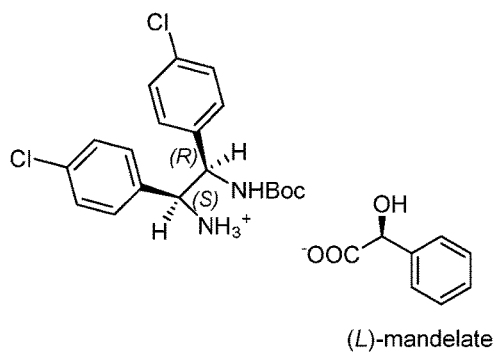
Figure 1A:
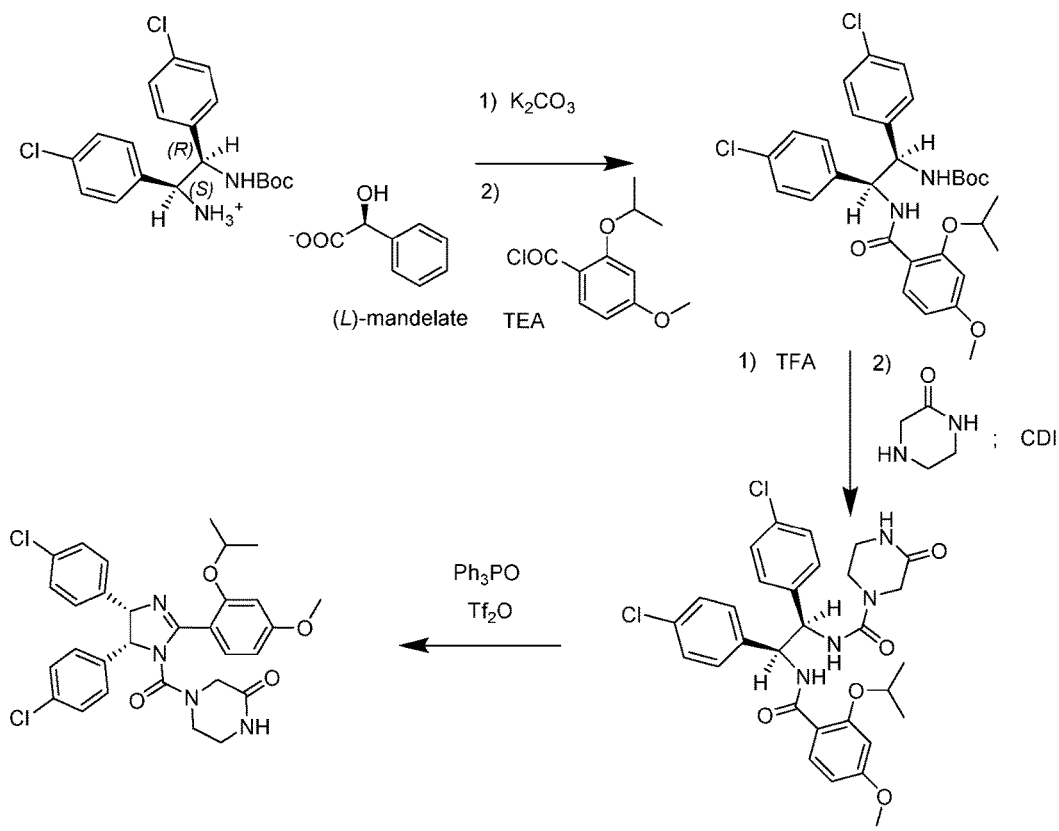
Figure 1B:
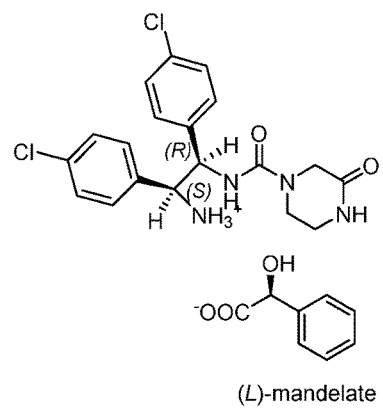
Figure 1B:
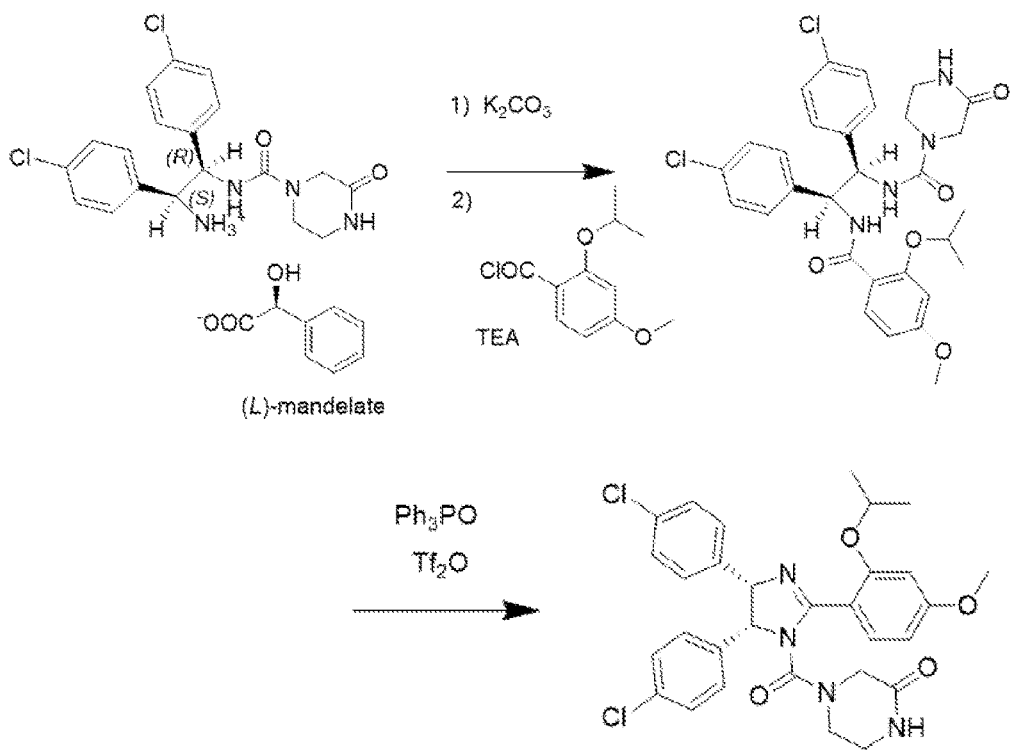
Figure 1C:
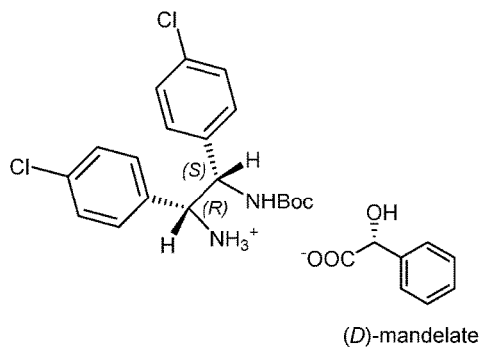
Figure 1C:
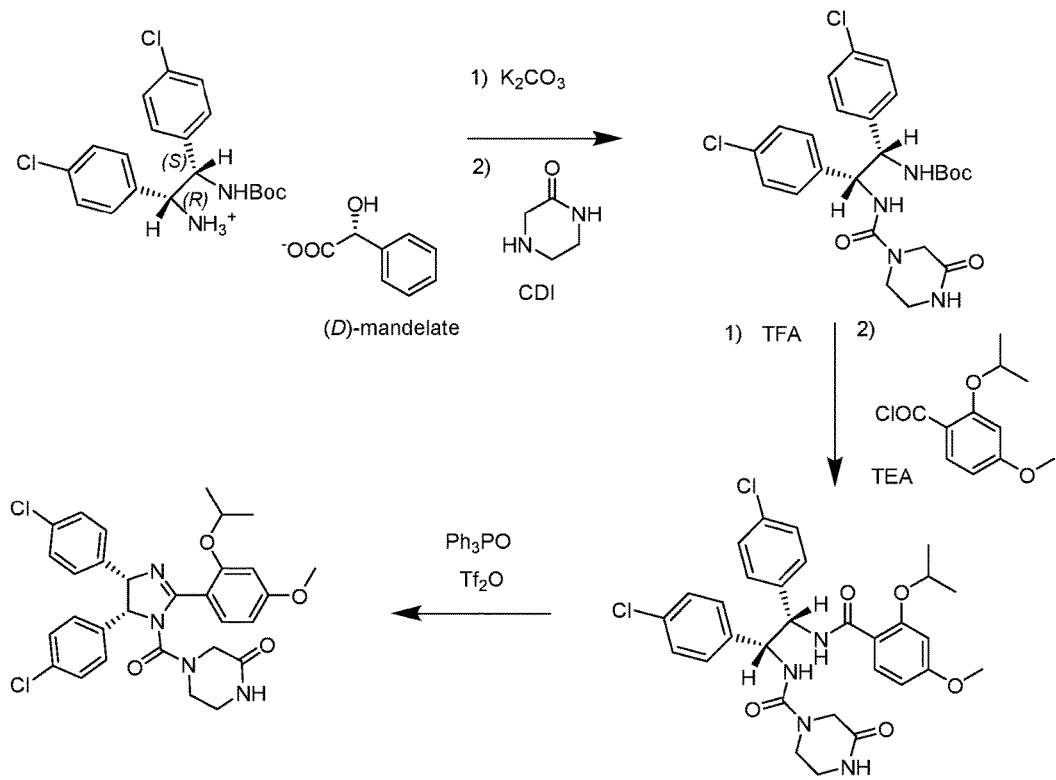
Figure 1D:
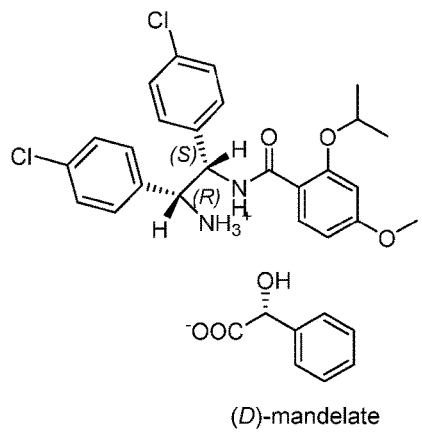
Figure 1D:
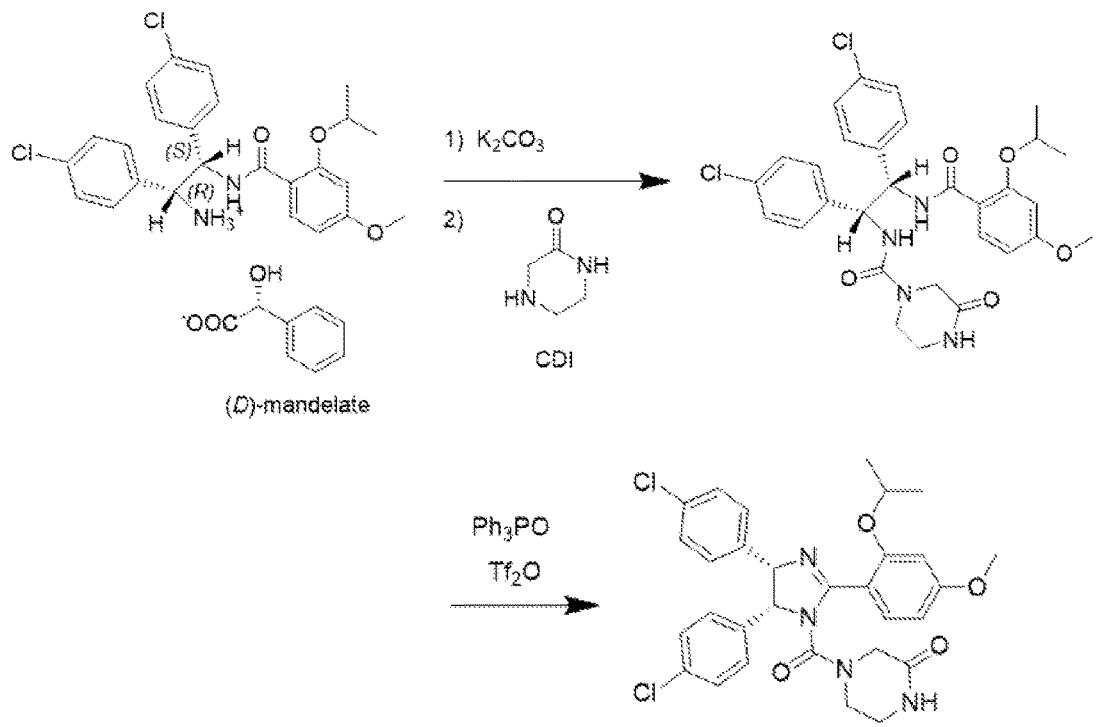

FIGS. 1(A), 1(B), 1(C) and 1(D) provide a non-limiting example of how the synthetic methods of this invention can be used to generate Nutlin-3a. The schemes are generalizable as appropriate to prepare other cis-imidazolines. A precursor is provided that has two substituted aryl groups attached to the two chiral centers in ethylene diamine. One of the two amines is either protected with an amine protected group, as shown in FIGS. 1(A) and 1(C), or derivatized towards the target cis-imidazoline, Nutlin-3a, as shown in FIGS. 1(B) and 1(D). The racemic mixture is separated using a chiral aromatic acid such as mandelic acid in either the D- or the L-form, as appropriate.

After separation, the synthesis continues via selective derivatization of the two amine groups in A, followed by ring closure to form the central imidazoline structure. If the chirally separated precursor A has an amine derivatized as a urea, then the free amine is converted to an amide via acylation, and vice versa. If the chirally separated precursor has a free amine and a protected amine, then the free amine is converted first to a urea or an amide, depending on the absolute stereochemistry of the precursor. The other amine is then deprotected and derivatized with the other reagent. The cis-imidazoline ring is then closed, ultimately producing the target cis-imidazoline, Nutlin-3.

Suitable Precursors for Chiral Resolution

In general terms, the invention includes synthetic method according to the following structures and schemes. For example, the invention provides a method of making a salt according to Formula (II) or Formula (IV):

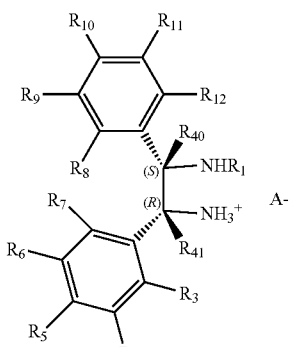

(II)

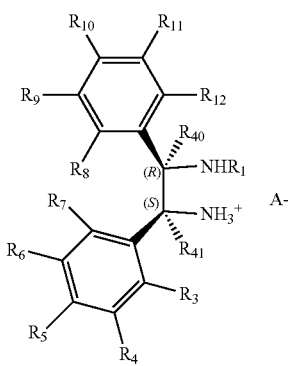

(IV)

The method comprises contacting a compound according to Formula (I):

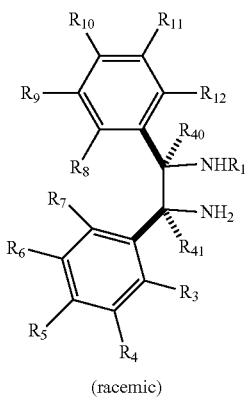

(I)

(racemic)

with a chiral acid (H-A) under salt-forming conditions, thereby producing a compound of Formula (II) or Formula (IV) in 80% ee (enantiomeric excess) or greater, wherein $A^-$ is a conjugate base of the chiral acid; and wherein:

$R^1$ is selected from

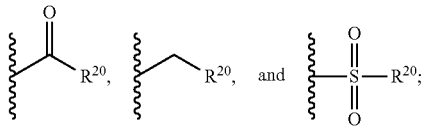

$R^{20}$ is selected from —$OCH_2R^{30}$, —$OR^{30}$; $C_{1-10}$ alkyl; and $C_{3-10}$ carbocycle and 3- to 10-membered heterocycle, wherein each $C_{3-10}$ carbocycle and 3- to 10-membered heterocycle in $R^{20}$ is optionally substituted with one or more substituents selected from halogen, —$OR^{30}$, —$SR^{30}$, —$N(R^{30})_2$, —$S(O)R^{30}$, —$S(O)_2R^{30}$—$C(O)R^{30}$, —$C(O)OR^{30}$, —$OC(O)R^{30}$, —$NO_2$, $=O$, $=S$, $=N(R^{30})$, —$P(O)(OR^{30})_2$, —$OP(O)(OR^{30})_2$, —$CN$, $C_{1-6}$ alkyl, $C_{2-6}$ alkenyl, and $C_2$ alkynyl;

$R^{30}$ is independently selected at each occurrence from hydrogen; and $C_{1-10}$ alkyl, $C_{2-10}$ alkenyl, $C_{2-10}$ alkynyl, $C_{3-15}$ carbocycle, and 3- to 10-membered heterocycle, each of which is independently optionally substituted at each occurrence with one or more substituents selected from halogen, —$CN$, —$NO_2$, $=O$, $=S$, and haloalkyl; $R^{46}$ and $R^{41}$ are independently selected at each occurrence from hydrogen and $C_{1-10}$ alkyl;

$R^3$, $R^4$, $R^5$, $R^6$, and $R^7$ are independently selected at each occurrence from hydrogen, halogen, —$OR^{100}$, —$SR^{100}$, —$N(R^{100})_2$, —$S(O)R^{100}$, —$S(O)_2R^{100}$, —$C(O)R^{100}$, —$C(O)OR^{100}$, —$OC(O)R^{100}$, —$NO_2$, —$P(O)(OR^{100})_2$, —$OP(O)(OR^{100})_2$ and —$CN$; $C_{1-10}$ alkyl, $C_{2-10}$ alkenyl, $C_{2-10}$ alkynyl, each of which is independently optionally substituted at each occurrence with one or more substituents selected from halogen, —$OR^{100}$, —$S(O)R^{100}$, —$S(O)_2R^{100}$, —$C(O)R^{100}$, —$C(O)OR^{100}$, —$OC(O)R^{100}$, —$NO_2$, $=O$, $=S$, $=N(R^{100})$, —$P(O)(OR^{100})_2$, —$OP(O)(OR^{100})_2$, —$CN$, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^3$, $R^4$, $R^5$, $R^6$, and $R^7$ is independently optionally substituted with one or more substituents selected from halogen, —$OR^{100}$, —$SR^{100}$, —$N(R^{100})_2$, —$S(O)R^{100}$, —$S(O)_2R^{100}$—$C(O)R^{100}$, —$C(O)OR^{100}$, —$OC(O)R^{100}$, —$NO_2$, $=O$, $=S$, $=N(R^{100})_2$, —$P(O)(OR^{100})_2$, —$OP(O)(OR^{100})_2$, —$CN$, $C_{1-6}$ alkyl, $C_{2-6}$ alkenyl, and $C_{2-6}$ alkynyl;

$R^8$, $R^9$, $R^{10}$, $R^{11}$, and $R^{12}$ are independently selected at each occurrence from hydrogen, halogen, —$OR^{100}$, —$SR^{100}$, —$N(R^{100})_2$, —$S(O)R^{100}$, —$S(O)_2R^{100}$, —$C(O)R^{100}$, —$C(O)OR^{100}$, —$OC(O)R^{100}$, —$NO_2$, —$P(O)(OR^{100})_2$, —$OP(O)(OR^{100})_2$ and —$CN$; $C_{1-10}$ alkyl, $C_{2-10}$ alkenyl, $C_{2-10}$ alkynyl, each of which is independently optionally substituted at each occurrence with one or more substituents selected from halogen, —$OR^{100}$, —$SR^{100}$, —$N(R^{100})_2$, —$S(O)R^{100}$, —$S(O)_2R^{100}$, —$C(O)R^{100}$, —$C(O)OR^{100}$, —$OC(O)R^{100}$, —$NO_2$, $=O$, $=S$, $=N(R^{100})$, —$P(O)(OR^{100})_2$, —$OP(O)(OR^{100})_2$, —$CN$, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^8$, $R^9$, $R^{10}$, $R^{11}$, and $R^{12}$ is independently optionally substituted with one or more substituents selected from halogen, —$OR^{100}$, —$SR^{100}$, —$N(R^{100})_2$, —$S(O)R^{100}$, —$S(O)_2R^{100}$—$C(O)R^{100}$, —$C(O)OR^{100}$, —$OC(O)R^{100}$, —NO$_2$, =O, =S, =N(R$^{100}$), —P(O)(OR$^{100}$)$_2$, —OP(O)(OR$^{100}$)$_2$, —CN, C$_{1-6}$ alkyl, C$_{2-6}$ alkenyl, and C$_{2-6}$ alkynyl; and R$^{100}$ at each occurrence is independently selected from hydrogen; and C$_{1-10}$ alkyl, C$_{2-10}$ alkenyl, C$_{2-10}$ alkynyl, C$_{3-10}$ carbocycle, and 3- to 10-membered heterocycle each of which is independently optionally substituted at each occurrence with one or more substituents selected from halogen, —CN, —NO$_2$, =O, =S, and haloalkyl.

When R$^1$ is

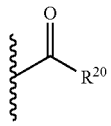

and R$^{20}$ is an optionally substituted saturated 5- or 6-membered heterocycle, then R$^1$ can be

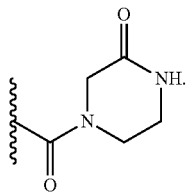

When R$^{20}$ is an optionally substituted C$_{3-10}$ carbocycle substituted with one or more substituents selected from halogen, —OR$^{30}$, —SR$^{30}$, —N(R$^{30}$)$_2$, —C(O)R$^{30}$, —C(O)OR$^{30}$, —OC(O)R$^{30}$, —NO$_2$, =O, =S, —CN, C$_{1-6}$ alkyl, C$_{2-6}$ alkenyl, and C$_{2-6}$ alkynyl, then R$^1$ can be selected from

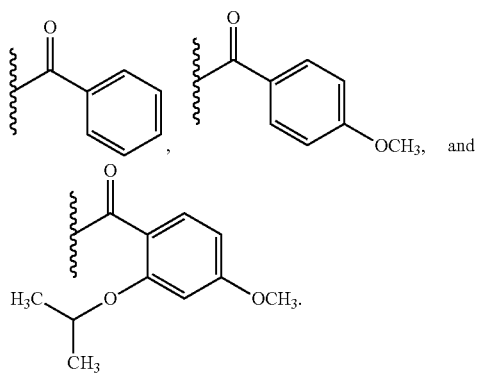

When R$^{20}$ is an —OCH$_2$R$^{30}$, —OR$^{30}$, or optionally substituted C$_{1-10}$ alkyl, then R$^1$ can be selected from

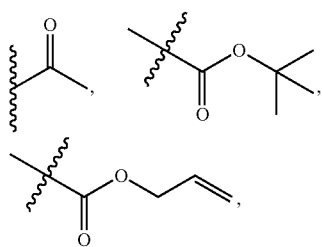

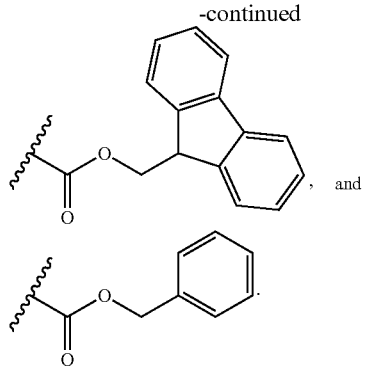

When R$^1$ is

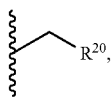

then R$^{20}$ can be an optionally substituted C$_{3-10}$ carbocycle substituted with one or more substituents selected from halogen, —OR$^{30}$, —SR$^{30}$, —N(R$^{30}$)$_2$, —C(O)R$^{30}$, —C(O)OR$^{30}$, —OC(O)R$^{30}$, —NO$_2$, =O, =S, —CN, C$_{1-6}$ alkyl, C$_{2-6}$ alkenyl, and C$_{2-6}$ alkynyl. When R$^1$ is

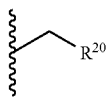

and R$^{20}$ is an optionally substituted phenyl, then R$^1$ can be selected from

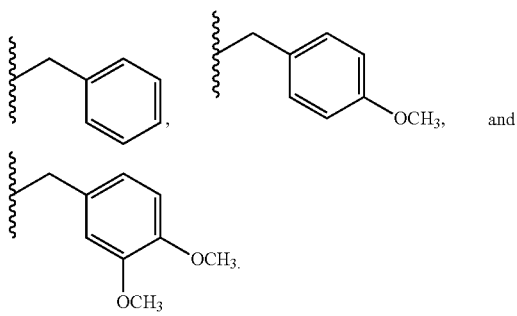

When R$^1$ is

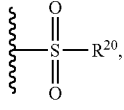

then R$^{20}$ can be an optionally substituted C$_{3-10}$ carbocycle substituted with one or more substituents selected from halogen, —OR$^{30}$, —SR$^{30}$, —N(R$^{30}$)$_2$, —C(O)R$^{30}$, —C(O)OR$^{30}$, —OC(O)R$^{30}$, —NO$_2$, =O, =S, —CN, C$_{1-6}$ alkyl, C$_{2-6}$ alkenyl, and C$_{2-6}$ alkynyl. When R$^{20}$ is an optionally substituted phenyl, then R$^1$ can be selected from

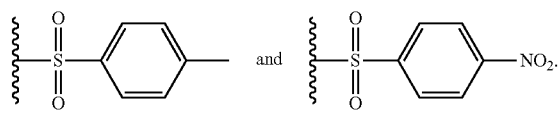 [SMILES: *S(=O)(=O)c1ccc(C)cc1 ; *S(=O)(=O)c1ccc([N+](=O)[O-])cc1]

Suitable Chiral Acids for Resolving a Chiral Precursor from its Enantiomer

To resolve a racemic mixture of Formula (II) or (IV), it is combined with a chiral acid which preferentially forms a salt or crystal with one of the two stereoisomers. The salts are separated from the remaining liquid, thereby separating one stereoisomer from the other. Either or both of the resolved chiral precursors can then be used to produce the desired cis-imidazoline.

The chiral acid may be selected from commercially available optically pure reagents. It may be represented by Formula (III) or Formula (V):

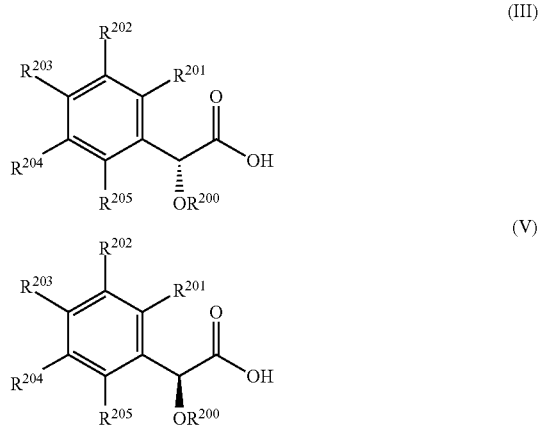

wherein $R^{200}$ is selected from hydrogen; and $C_{1-10}$ alkyl, $C_{2-10}$ alkenyl, $C_{2-10}$ alkynyl, $C_{3-10}$ carbocycle, and 3- to 10-membered heterocycle each of which is independently optionally substituted at each occurrence with one or more substituents selected from halogen, —CN, —NO$_2$, =O, =S, and haloalkyl; and $R^{201}$, $R^{202}$, $R^{203}$, $R^{204}$, and $R^{205}$ are independently selected at each occurrence from hydrogen, halogen, —OR$^{100}$, —SR$^{100}$, —N(R$^{100}$)$_2$, —S(O)R$^{100}$, —S(O)$_2$R$^{100}$, —C(O)R$^{100}$, —C(O)OR$^{100}$, —OC(O)R$^{100}$, —NO$_2$, —P(O)(OR$^{100}$)$_2$, —OP(O)(OR$^{100}$)$_2$ and —CN; $C_{1-10}$ alkyl, $C_{2-10}$ alkenyl, $C_{2-10}$ alkynyl, each of which is independently optionally substituted at each occurrence with one or more substituents selected from halogen, —OR$^{100}$, —SR$^{100}$, —N(R$^{100}$)$_2$, —S(O)R$^{100}$, —S(O)$_2$R$^{100}$, —C(O)R$^{100}$, —C(O)OR$^{100}$, —OC(O)R$^{100}$, —NO$_2$, =O, =S, =N(R$^{100}$), —P(O)(OR$^{100}$)$_2$, —OP(O)(OR$^{100}$)$_2$, —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^8$, $R^9$, $R^{10}$, $R^{11}$, and $R^{12}$ is independently optionally substituted with one or more substituents selected from halogen, —OR$^{100}$, —SR$^{100}$, —N(R$^{100}$)$_2$, —S(O)R$^{100}$, —S(O)$_2$R$^{100}$—C(O)R$^{100}$, —C(O)OR$^{100}$, —OC(O)R$^{100}$, —NO$_2$, =O, =S, =N(R$^{100}$), —P(O)(OR$^{100}$)$_2$, —OP(O)(OR$^{100}$)$_2$, —CN, $C_{1-6}$ alkyl, $C_{2-6}$ alkenyl, and $C_{2-6}$ alkynyl.

For example, the chiral acid may be:

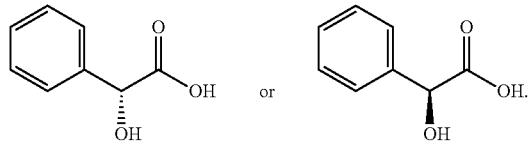 [SMILES: O=C(O)[C@H](O)c1ccccc1 ; O=C(O)[C@@H](O)c1ccccc1]

Testing Biological Activity

Compounds can be screened on the molecular level for their ability to act as agonists of MDM2, thereby promoting p53 activity and causing senolysis. Example C provides an illustration of an assay for this purpose.

Compounds can also be screened for their ability to kill or alter the phenotype of target cells in a cell population. Cultured cells are contacted with the compound, and the degree of cytotoxicity or inhibition of the cells is determined. The ability of the compound to kill or inhibit target cells can be compared with the effect of the compound on a control cell type. Where the target cells are cancer cells, the control cells can be non-cancerous cells of the same tissue origin, or normal cells that are typically in the environment where the compound is administered. Where the cells are senescent cells, the control cells can be cells that are freely dividing at low density, and/or normal cells that are in a quiescent state at high density. Example D provides an illustration using the human lung fibroblast IMR90 cell line. Similar protocols are available for testing the ability of the cells to kill or inhibit cancer cells and other types of target cells.

Compounds can also be tested for their ability to improve the course of diseases and other conditions thought to be caused or mediated by senescent cells. See US 2016/0339019 A1.

Purity

When a cis-imidazoline is prepared according to this invention, it can be produced with a high degree of enantiomeric purity. For example, depending on the compounds and methods used, the compound of Formula (II) or Formula (IV) can be produced with an enantiomeric excess (ee) of at least 80%, 90%, 95%, 98%, or 99%. The enantiomeric excess can be enriched through recrystallization of the crude salt, to achieve the desired enantiopurity. The amounts of the racemic mixture and the chiral acid used in enantioselectivity will depend on the properties of the particular racemic mixture and chiral acid. Generally, the racemic mixture is contacted with the chiral acid in a mole ratio of about 3:1 to about 0.5:1, or about 3:1 to about 1:1. A judicious choice of crystallization solvents, temperatures, and other conditions will facilitate the enantio-enrichment process.

Incorporation of Deuterium and Use in Biological Assays

Optionally, the synthetic methods of this invention can be used to produce cis-imidazolines labeled, for example, with stable isotopes. Through a careful choice of reagents, the isotopic label may be incorporated in several sites of the target cis-imidazoline, in a regio-controlled manner. Example B of this disclosure provides an illustration in which 7 deuterium atoms are incorporated by way of deuterated 2-isopropoxy-4-methoxybenzoic acid.

Such labeled compounds can be used, for example, as internal standards in a quantitative assay. For example, to determine Nutlin-3a concentrations in a plasma sample, the plasma is spiked with a pre-determined amount of [D$^7$] Nutlin-3a, and then acetonitrile is added to precipitate the protein. The supernatant contains extracted Nutlin-3a (comprising both the Nutlin-3a in the original sample that is to be measured, and the [D$^7$]Nutlin-3a internal standard). The supernatant is analyzed by ultra-high pressure liquid chromatography with tandem mass spectrometry (UHPLC/MS/MS). The ratio of Nutlin-3a peak area to [D$^7$]Nutlin-3a peak area and the theoretical concentrations of the calibration samples are fit to a regression model from which the original plasma sample can be back calculated.

Preparation of Pharmaceutical Compositions and their Use

Cis-imidazolines prepared according to the synthetic methods of this invention may be formulated into a pharmaceutical composition or medicament, for example, by combining with one or more suitable excipients and/or placing in a device to facilitate administration. Materials and methods suitable for preparing such medicaments may be found, for example, in the most recent edition of *Remington: The Science and Practice of Pharmacy* (currently in the 22$^{nd}$ edition), and other standard reference sources. Such a medicament or composition may be packaged with or accompanied by information about its use in clinical medicine. Depending on the circumstances, the medicaments and pharmaceutical compositions of this invention may be suitable for administration to a patient in need thereof for purposes of treating or alleviating the symptoms of a condition such as cancer or a condition caused or mediated by senescent cells.

Definitions

The term "cis-imidazoline" is used throughout this disclosure to refer to a target compound of the synthetic methods of this invention. The term is used for convenience and by way of example, and does not confer any limitation on the claimed invention that is beyond what is explicitly stated or otherwise required. To the extent possible, the term cis-imidazoline as it is used in this disclosure may be replaced mutatis mutandis with the more general term "compound" or "structure." Unless explicitly stated or otherwise required, the use of any compound in this disclosure includes use of the conjugate base or acid (optionally in salt form) as an alternative or in addition to the structure shown.

A "senescent cell" is generally thought to be derived from a cell type that typically replicates, but as a result of aging or other event that causes a change in cell state, can no longer replicate. It remains metabolically active and commonly adopts a senescence associated secretory phenotype (SASP). The nucleus of senescent cells is often characterized by senescence-associated heterochromatin foci and DNA segments with chromatin alterations reinforcing senescence. Without implying any limitation on the practice of what is claimed in this disclosure that is not explicitly stated or required, the invention is premised on the hypothesis that senescent cells cause or mediate certain conditions associated with tissue damage or aging. For the purpose of practicing aspects of this invention, senescnet cells can be identified as expressing at least one marker selected from p16, senescence-associated β-galactosidase, and lipofuscin; sometimes two or more of these markers, and optionally other markers of SASP such as interleukin 6.

A "senescence associated" disease, disorder, or condition is a physiological condition that presents with by one or more symptoms or signs, wherein a subject having the condition needs or would benefit from a lessening of such symptoms or signs. The condition is senescence associated if it occurs predominantly in people over 65 years of age, or if it is caused or mediated by senescent cells. Lists of senescence associated disorder that can potentially be treated or managed using cis-imidazolines according to this invention include conditions described in US 2016/0339019 A1 (Laberge et al.) and/or in WO 2017/008060 (López-Dominguez et al.), including but not limited to osteoarthritis.

A "chiral aromatic acid" referred to in this disclosure is one of two possible enantiomers of an aromatic amino acid. Where neither of the two enantiomers is explicitly referred to, depicted, or otherwise required, the term refers alternately to either one or the other enantiomer but not both together.

Compounds of the invention include the compounds depicted, and/or crystalline and amorphous forms, pharmaceutically acceptable salts, solvates, hydrates, and polymorphs thereof in any combination, unless such other forms of the compound are excluded.

A "precursor" or "intermediate" is a structure that is synthesized, purchased, or otherwise acquired that may be subject to one or more chemical reaction steps and/or separation steps that change the structure and/or separate components of a reaction mixture to yield a desired target compound, such as a cis-imidazoline.

A "protecting group" is introduced into a molecule by chemical modification of a functional group to obtain chemoselectivity in a subsequent chemical reaction. Representative removable amine protecting groups include but are not limited to carbobenzyloxy (Cbz), p-Methoxybenzyl carbonyl (Moz or MeOZ), tert-Butyloxycarbonyl (BOC), 9-Fluorenylmethyloxycarbonyl (FMOC), Allyloxycarbonyl (Alloc), Benzoyl (Bz), p-Methoxybenzyl (PMB), 3,4-Dimethoxybenzyl (DMPM), p-methoxyphenyl (PMP), and Tosyl (Ts).

The term "enantiomeric excess" or "ee" refers to the purity of a chiral substance. In particular, enantiomeric excess reflects the degree to which a material contains one enantiomer in greater amounts than other enantiomers. A racemic mixture has an ee of 0%, while a single pure enantiomer has an ee of 100%.

The term "salt" or "pharmaceutically acceptable salt" refers to a salt derived from pharmaceutically compatible organic and/or inorganic counter-ions of the compound referred to.

The term "$C_{x-y}$" when used in conjunction with a chemical moiety, such as alkyl, alkenyl, or alkynyl is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond respectively.

The term "carbocycle" refers to a saturated, unsaturated or aromatic ring in which each atom of the ring is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. By way of example, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary carbocycles include cyclopentyl, cyclohexyl, cyclohexenyl, adamantyl, phenyl, indanyl, and naphthyl.

The term "heterocycle" refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings wherein at least one of the rings includes a heteroatom. By way of example, an aromatic ring, e.g., pyridyl, may be fused to a saturated or unsaturated ring, e.g., cyclohexane, cyclopentane, morpholine, piperidine or cyclohexene.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also include polycyclic ring systems having two or more cyclic rings in which two or more carbons are common to two adjoining rings wherein at least one of the rings is heteroaromatic, e.g., the other cyclic rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities referred to are intended to include all Z-, E- and tautomeric forms.

The term "substituted" refers to moieties having substituents replacing a hydrogen on one or more carbons of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, and elimination.

The term "substituted" includes all permissible substituents of organic compounds. The permissible substituents include acyclic and cyclic, branched and unbranched, carbocyclic and heterocyclic, aromatic and non-aromatic substituents of organic compounds. The heteroatoms such as nitrogen may have hydrogen substituents and/or any permissible substituents of organic compounds that satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety Substituents may include, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

Substituents can themselves be substituted, if appropriate. Unless specifically stated as "unsubstituted," references to chemical moieties include substituted variants. For example, reference to a "heteroaryl" group or moiety implicitly includes both substituted and unsubstituted variants.

Other terms used in this disclosure have their ordinary meaning, as would be understood by a person of ordinary skill in the art in which this invention is put into practice.

EXAMPLES

Example A: Preparation of an Exemplary Cis-Imidazoline

Figure 2A:
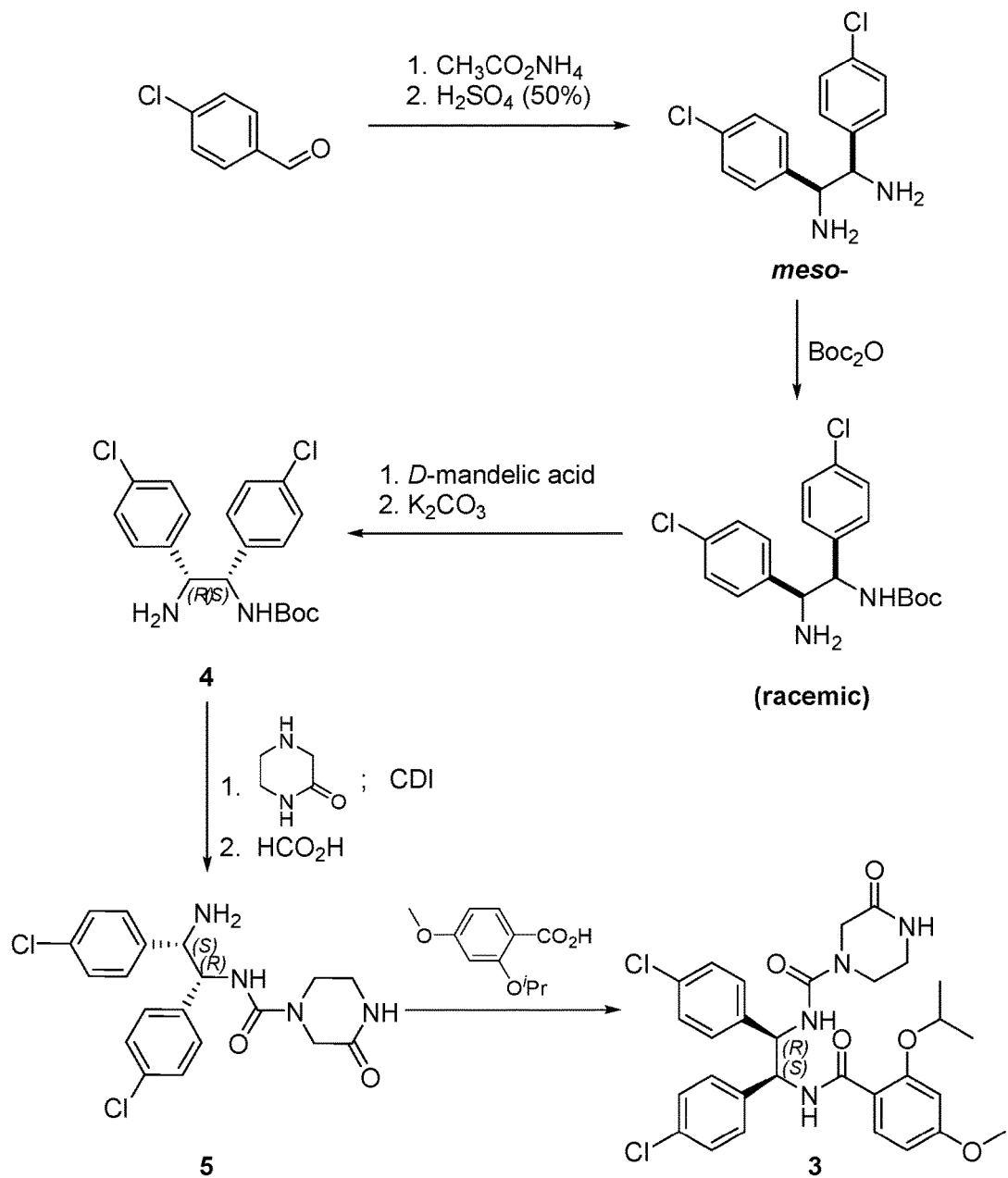
Figure 2B:
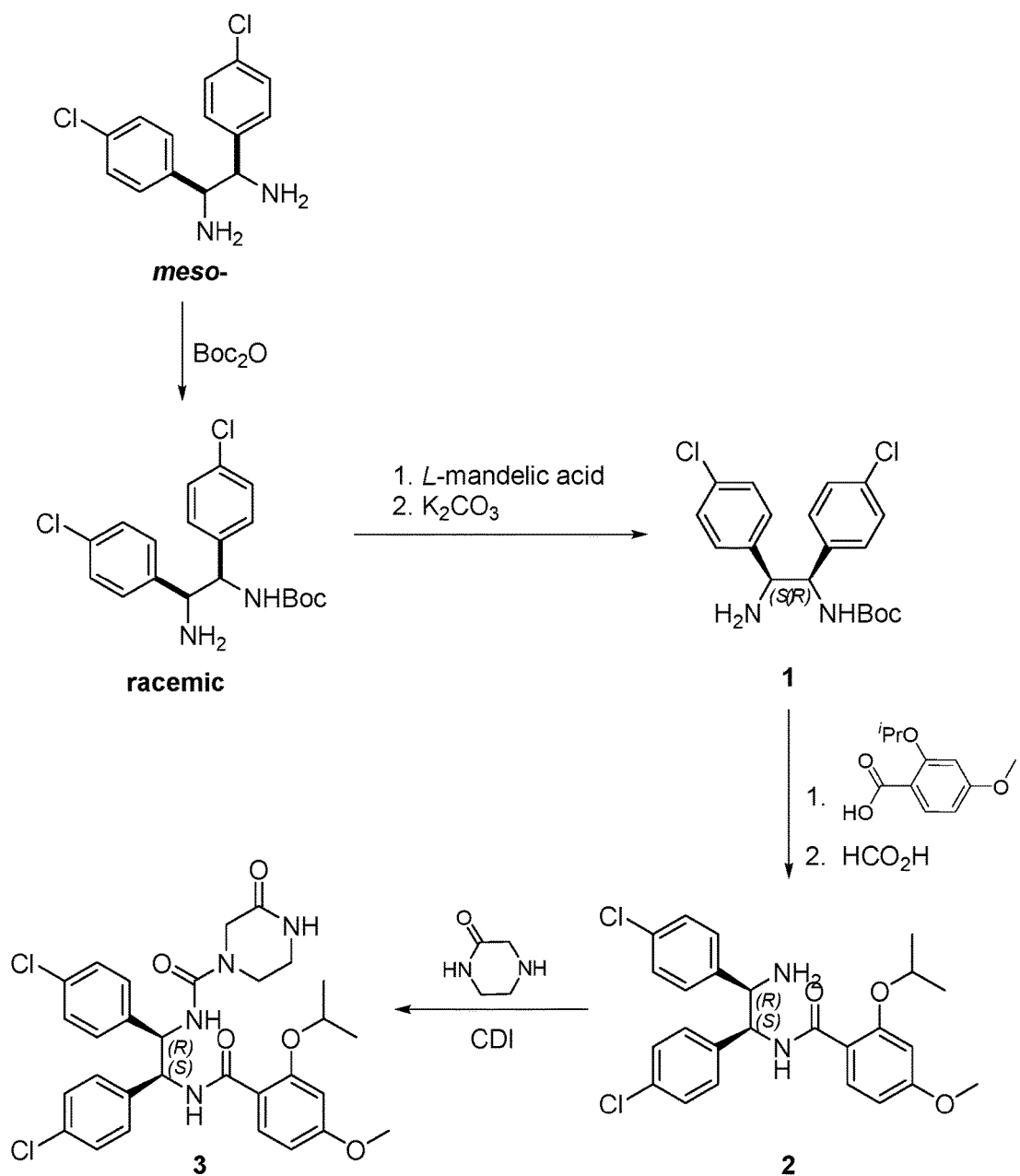
Figure 2C:
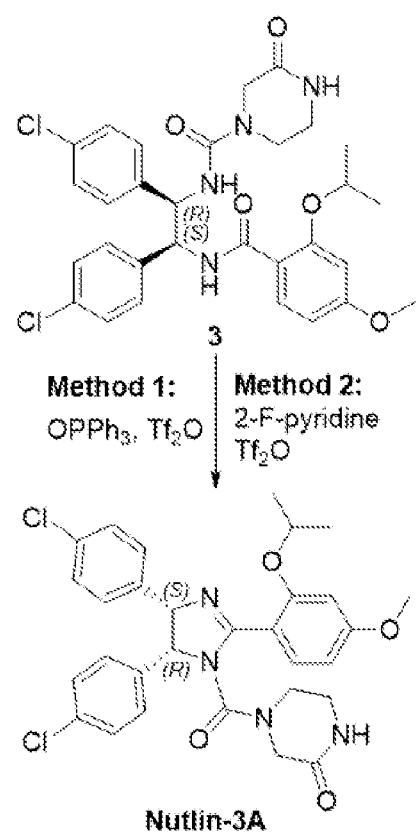
Figure 3:
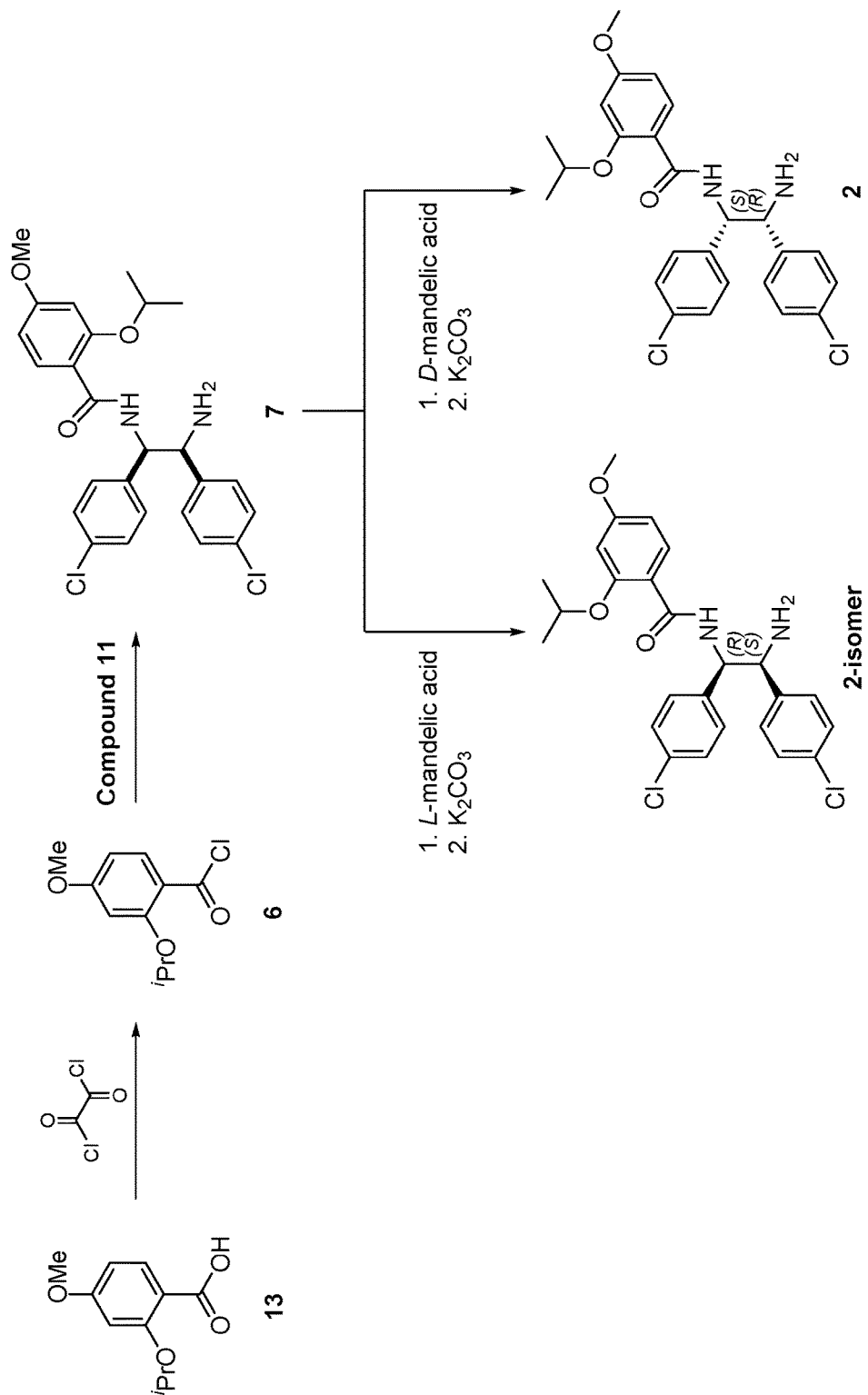
FIG. 3 shows an alternative route to Compound 2.

FIGS. 2(A), 2(B), and 2(C) show a synthetic scheme for the cis-imidazoline Nutlin-3a, as a non-limiting illustration of this invention in operation. FIG. 3 shows an alternative route to Compound 2. The procedure used was as follows.

Protocol 1: Synthesis of 1,2-Bis(4-chlorophenyl)ethane-1,2-diamine (Compound 11)

By modification of the method of Wein, M. et al. Cancer Res. Clin. Oncol. 1988, 114, 347-58, a mixture of 4-chlorobenzaldehyde (2.90 g, 20.6 mmol) (Compound 10) and CH$_3$CO$_2$NH$_4$ (349 mg, 4.5 mmol) was heated at 120° C. for 3 h. The reaction mixture was cooled to room temperature and then poured into EtOAc/H$_2$O (150 mL/150 mL). The two phases were separated and the organic phase was washed with 5% NaOH (150 mL). The EtOAc phase was dried over anhydrous Na$_2$SO$_4$ and concentrated. The residue was washed with petroleum ether (50 mL) and filtered to afford N-[1,2-bis(4-chlorophenyl)-2-[(E)-(4-chlorophenyl)methyleneamino]ethyl]-4-chloro-benzamide (2.61 g, 93% yield) as white solid, which was used in the next step without further purification.

N-[1,2-bis(4-chlorophenyl)-2-[(E)-(4-chlorophenyl)methyleneamino]ethyl]-4-chloro-benzamide (2.61 g, 4.8 mmol) was suspended in 50% H$_2$SO$_4$ (30 mL). The reaction mixture was heated at 180° C. for 3 h. When cooled to room temperature, the mixture was diluted with ice water (20 mL) and the resulting mixture was extracted with EtOAc (3×50 mL). The aqueous phase was basified with NH$_4$OH (Conc.)

and extracted with Et$_2$O (3×50 mL). The combined organic phases were washed with brine (2×20 mL), dried over anhydrous Na$_2$SO$_4$ and concentrated. The residue was purified by column chromatography on silica gel to afford Compound 11 (553 mg, 41% yield) as white solid. MS (ESI) m/z=281.5 [M+H]$^+$. $^1$H NMR (400 M, DMSO-d$_6$), δ 7.28 (m, 4H), 7.16 (m, 4H), 3.93 (s, 2H), 1.95 (br, s, 4H). $^{13}$C NMR (100 M, DMSO-d6), δ 143.1, 131.4, 129.8, 127.9, 61.6.

Protocol 2: Synthesis of tert-Butyl-2-amino-1,2-bis (4-chlorophenyl)ethyl) carbamate (Compound 12)

To a solution of Compound 11 (1.01 g, 3.6 mmol) in DCM (20 mL), Boc$_2$O (765 mg, 3.5 mmol) was added at 0° C. The reaction mixture was stirred at this temperature for 2 h, and then quenched with water (15 mL). The two phases were separated and the aqueous phase was further extracted with DCM (15 mL×2). The combined organic phases were washed with water (15 mL), dried over anhydrous Na$_2$SO$_4$ and concentrated to afford Compound 12 (1.32 g, 96% yield) as white solid, which was used in the next step without further purification. MS (ESI) m/z=381.4 [M+H]$^+$. $^1$H NMR (400 M, DMSO-d$_6$), δ 7.38-7.30 (m, 8H), 4.52 (m, 1H), 3.96 (m, 1H), 1.20 (m, 9H).

Protocol 3: Chemical Resolution-Synthesis of Compound 1 and Compound 4

To a solution of Compound 12 (2.61 g, 6.9 mmol) in THF (52 mL), D-mandelic acid (546 mg, 3.6 mmol) was added at room temperature. The mixture was stirred at 70° C. for 30 min, and then stirred at room temperature for 1 h and 0° C. for 30 min. After filtration, the filtration cake was collected (1.14 g, 89% ee) and further crystallized from THF (22 mL) to give Compound 4-salt (918 mg, >99% ee) as white crystal which was freed from saturated aq. Na$_2$CO$_3$ to give Compound 4 (610 mg, yield 23%) as white solid. The filtrate was concentrated, and the residue was poured into a mixture of EtOAc/sat. aqueous Na$_2$CO$_3$ (50 mL/50 mL). The resulting two phases were separated and the organic phase was collected, dried over anhydrous Na$_2$SO$_4$, and concentrated. The residue (1.46 g, 3.8 mmol, 50% ee) was dissolved in THF (30 mL) followed by addition of L-mandelic acid (400 mg, 2.6 mmol). This mixture was heated at 70° C. for 1 hour, and then stirred at room temperature for 2 hours and 0° C. for 30 min. The resulting mixture was filtered and the filtration cake was collected (1.04 g, 91% ee) and further crystallized from THF (20 mL) to afford Compound 1-salt (660 mg, >99% ee) as white crystal which was again freed from saturated aq. Na$_2$CO$_3$ to give Compound 1 (415 mg, yield 16%) as white solid.

Alternatively the order of these two resolution steps can be reversed, to give Compound 1-salt as a crystalline solid from Compound 12 and L-mandelic acid; the residue is then treated with D-mandelic acid to recover Compound 4-salt as a white crystalline product.

Protocol 4: Synthesis of N-[(1S,2R)-2-amino-1,2-bis(4-chlorophenyl)ethyl]-2-isopropoxy-4-methoxy-benzamide (Compound 2)

To a solution of 2-isopropoxy-4-methoxy-benzoic acid (194 mg, 923 μmol) in DCM (15 mL) were added DIPEA (238 mg, 1.84 mmol) and HATU (1.05 g, 2.76 mmol) at 0° C. The mixture was stirred at 0° C. for 30 min and then Compound 1 (351 mg, 921 μmol) was added. The reaction mixture was stirred at room temperature overnight. Water (20 mL) was added and the resulting mixture was extracted with DCM (30 mL×3). The combined organic phases were dried over anhydrous Na$_2$SO$_4$ and concentrated. The residue was purified by flash column chromatography on silica gel (DCM:MeOH=501) to afford Boc-Compound 2 (321 mg, 61% yield) as white solid. LCMS (ESI) m/z=573.1 [M+H]$^+$. $^1$H NMR (400 MHz, DMSO-d$_6$): 8.28 (m, 1H), 7.52 (m, 1H), 7.40 (m, 9H), 6.57 (m, 1H), 6.51 (m, 1H), 5.41 (m, 1H), 4.94 (m, 1H), 4.69 (m, 1H), 3.75 (s, 3H), 1.20 (m, 15H). [α]$_D$=−34° (c=0.40, CHCl$_3$)

To a solution of Boc-Compound 2 (460 mg, 802 μmol) in DCM (8 mL), HCO$_2$H (1.00 g, 8.77 mmol) was added. The reaction mixture was stirred at room temperature for 3 h and then concentrated. The residue was poured into water (50 mL) and the resulting mixture was adjusted to pH 9. This mixture was then extracted with DCM (15 mL×2) and the combined organic phases were washed with brine (10 mL), dried over Na$_2$SO$_4$ and concentrated to afford Compound 2 (350 mg, 92% yield) as yellow oil, which was used in next step without further purification. LCMS (ESI) m/z=found 472.9 [M+H]$^+$.

Protocol 5 Synthesis of 2-Isopropoxy-4-methoxybenzoyl chloride (Compound 6)

To a solution of 2-isopropoxy-4-methoxy-benzoic acid (400 mg, 1.90 mmol) in DCM (15 mL), oxalic dichloride (483 mg, 3.81 mmol) was added at 0° C., followed by one drop of DMF. The reaction mixture was stirred at 0° C. for 2 h, and then an excess of solvent was removed to afford crude Compound 6 which was used into the next step reaction without further purification.

Protocol 6: Synthesis of Cis-N-(2-amino-1,2-bis(4-chlorophenyl)ethyl)-2-isopropoxy-4-methoxybenz-amide (Compound 7)

To a mixture of Cis-1,2-bis(4-chlorophenyl)ethane-1,2-diamine (440 mg, 1.56 mmol) and Et$_3$N (253 mg, 2.51 mmol) in DCM (20 mL), Compound 6 was added and prepared above at 0° C. The reaction mixture was stirred at room temperature overnight. An excess of solvent was removed by concentration, and the residue was purified by column chromatography on silica gel (EtOAc:Hexane=2:1) to afford Compound 7 (512 mg, 65% yield). MS (ESI) m/z=474.8 [M+H]$^+$. $^1$H NMR (400 M, CDCl$_3$), δ 8.88 (m, 1H), 8.12 (d, J=8.8 Hz, 1H), 7.26-7.19 (m, 4H), 7.03-6.99 (m, 4H), 6.56 (dd, J$_1$=5.6 Hz, J$_2$=8.8 Hz, 1H), 6.49 (d, J=5.6 Hz, 1H), 5.44 (m, 1H), 4.76 (m, 1H), 4.41 (m, 1H), 3.83 (s, 3H), 1.44 (m, 6H).

Protocol 7: Synthesis of Compound 2 and Compound 2-Isomer

D-Mandelic acid (78 mg, 512.65 μmol) was added to a solution of Compound 7 (504 mg, 1.06 mmol) in THF (10 mL) at room temperature. The reaction mixture was stirred at room temperature for 1 h and then stirred at 0° C. for 45 min. The resulting mixture was filtered. The filtration cake (98 mg, ee 80%) was re-crystallized from MTBE/THF (3 mL/5 mL) to afford Compound 2-salt (25 mg, >99% ee) which was freed up by K$_2$CO$_3$ to afford free-base Compound 2. The filtrate was concentrated and then freed with aqueous K$_2$CO$_3$ (30 mL) to afford Compound 7 (442 mg, 934 μmol). This material was dissolved in THF (4 mL), and L-Mandelic acid (68 mg, 447 μmol) was added at room temperature. The reaction mixture was stirred at room temperature for 1 h and filtered. The filtration cake (148 mg, ee 91%) was re-crystallized from MTBE/THF (8 mL/2 mL) to afford Compound 2-isomer-salt (38 mg, >99% ee) which was also freed up by $K_2CO_3$ to afford free-base Compound 2-isomer.

Protocol 8: Synthesis of N-((1R,2S)-1,2-bis(4-chlorophenyl)-2-(2-isopropoxy-4-methoxybenzamido)ethyl)-3-oxopiperazine-1-carboxamide (Compound 3)

To a solution of Compound 2 (100 mg, 211 μmol) in DCM (8 mL), CDI (68 mg, 419 μmol) was added at 0° C. The reaction mixture was stirred at room temperature for 1 h. Piperazin-2-one (42 mg, 420 μmol) was added at room temperature and the reaction mixture was stirred at room temperature for 2 h. Water (10 mL) was added and the resulting mixture was extracted with EtOAc (10 mL×3). The combined organic phases were washed with brine (10 mL), dried over anhydrous $Na_2SO_4$ and concentrated to afford Compound 3 (83 mg, 66% yield) as white solid. LCMS (ESI) m/z=599.1 $[M+H]^+$. $^1H$ NMR (400 MHz, DMSO-$d_6$): 8.29 (m, 1H), 7.94 (s, 1H), 7.46 (m, 7H), 7.36 (m, 2H), 6.99 (m, 1H), 6.57 (m, 1H), 6.52 (m, 1H), 5.59 (m, 1H), 5.11 (m, 1H), 4.70 (m, 1H), 3.80 (m, 1H), 3.75 (s, 3H), 3.61 (m, 1H), 3.32 (m, 2H), 2.96 (m, 2H), 1.18 (m, 6H). $[\alpha]_D$=+88.7° (c=0.12, $CHCl_3$).

Protocol 9: Synthesis of N-((1R,2S)-2-amino-1,2-bis(4-chlorophenyl)ethyl)-3-oxopiperazine-1-carboxamide (Compound 5)

To a solution of Compound 4 (152 mg, 399 μmol) in DCM (10 mL), CDI (130 mg, 801 μmol) was added at 0° C. This mixture was stirred at room temperature for 1 h. Piperazin-2-one (80 mg, 799 μmol) was added and the reaction mixture was stirred at the same temperature for 2 h. Water (10 mL) was added and the resulting mixture was extracted with EtOAc (10 mL×3). The combined organic phases were washed with brine (10 mL), dried over anhydrous $Na_2SO_4$ and concentrated. The residue was purified by prep-TLC (DCM:MeOH=12:1) to afford Boc-Compound 5 (130 mg, 64% yield) as white solid. LCMS (ESI) m/z=529.1 $[M+Na]^+$. $^1H$ NMR (400 MHz, DMSO-$d_6$): 7.90 (s, 1H), 7.50 (m, 4H), 7.38 (m, 5H), 6.89 (m, 1H), 4.92 (m, 2H), 3.75 (m, 1H), 3.53 (m, 1H), 3.24 (m, 2H), 2.90 (m, 2H), 1.15 (s, 9H).

To a solution of Boc-Compound 5 (80 mg, 158 umol) in DCM (5 mL), TFA (360 mg, 3.16 mmol) was added. The reaction mixture was stirred at room temperature for 3 h and then concentrated. The residue was poured into water and the resulting mixture was adjusted to pH 9. The mixture was then extracted with DCM (15 mL×2). The combined organic phases were washed with brine (10 mL), dried over $Na_2SO_4$ and concentrated to afford Compound 5 (59 mg, 93% yield) as yellow oil, which was used in next step without further purification. LCMS (ESI) m/z=407.1 $[M+H]^+$.

Protocol 10: Synthesis of N-((1R,2S)-1,2-bis(4-chlorophenyl)-2-(2-isopropoxy-4-methoxybenzamido)ethyl)-3-oxopiperazine-1-carboxamide (Compound 3)

To a solution of Compound 5 (59 mg, 147 μmol) in DCM (5 mL), triethylamine (60 mg, 593 μmol) and dropwise a solution of 2-isopropoxy-4-methoxy-benzoyl chloride (51 mg, 219 μmol) in DCM (5 mL) were added at 0° C. The reaction mixture was stirred at room temperature for 1 h. Water (10 mL) was added and the resulting mixture was extracted with DCM (10 mL×3). The combined organic phases were washed with brine (10 mL), dried over anhydrous $Na_2SO_4$ and concentrated. The residue was purified with prep-TLC (DCM:MeOH=12:1) to afford Compound 3 (62 mg, 70% yield) as white solid. LCMS (ESI) m/z=599.1 $[M+H]^+$. $^1H$ NMR (400 MHz, DMSO-$d_6$): 8.29 (m, 1H), 7.94 (s, 1H), 7.46 (m, 7H), 7.36 (m, 2H), 6.99 (d, J=9.2 Hz, 1H), 6.57 (d, J=2.0 Hz, 1H), 6.52 (dd, J=8.8 Hz, 2.0 Hz, 1H), 5.60 (m, 1H), 5.11 (m, 1H), 4.70 (m, 1H), 3.80 (m, 1H), 3.75 (s, 3H), 3.61 (m, 1H), 3.32 (m, 2H), 2.96 (m, 2H), 1.18 (m, 6H).

Protocol 11: Synthesis of 4-[[(4S,5R)-4,5-Bis(4-chlorophenyl)-4,5-dihydro-2-[4-methoxy-2-(1-methylethoxy)phenyl]-H-imidazol-1-yl]carbonyl]-2-Piperazinone ((−)-Nutlin-3a)

To a solution of $Ph_3PO$ (120 mg, 432 μmol) in DCM (6 mL), $Tf_2O$ (240 mg, 850 μmol) was added dropwise at 0° C. The mixture was stirred at 0° C. for 30 min. A solution of Compound 3 (130 mg, 217 μmol) in DCM (2 mL) was added dropwise at 0° C. The reaction mixture was stirred at 0° C. for 1 h. The reaction mixture was concentrated and the residue was purified with prep-TLC (DCM:MeOH=11:1) to afford (−)-Nutlin-3a (83 mg, 62% yield) as white solid. LCMS (ESI) m/z=581.1 $[M+H]^+$. $^1H$ NMR (400 MHz, DMSO-$d_6$): 7.92 (s, 1H), 7.54 (m, 1H), 7.13 (m, 4H), 7.04 (m, 2H), 6.98 (m, 2H), 6.61 (m, 2H), 5.66 (m, 1H), 5.58 (m, 1H), 4.72 (m, 1H), 3.82 (s, 3H), 3.58 (m, 2H), 3.27 (m, 2H), 2.81 (s, 2H), 1.25 (m, 3H), 1.21 (m, 3H). $[\alpha]_D$=−140° (c=0.18, $CHCl_3$).

Protocol 12: Alternative Method of Synthesizing (−)-Nutlin-3a

To a solution of Compound 3 (29 mg, 48.37 μmol) and THF (1 mL) were added 2-fluoropyridine (23 mg, 236.89 mmol) and $Tf_2O$ (33 mg, 117.86 μmol) at 0° C. The reaction mixture was stirred at 40° C. overnight and then concentrated. The residue was purified by prep-HPLC to afford (−)-Nutlin-3a (6 mg, 18% yield).

Example B: Incorporation of Deuterium

Figure 4:
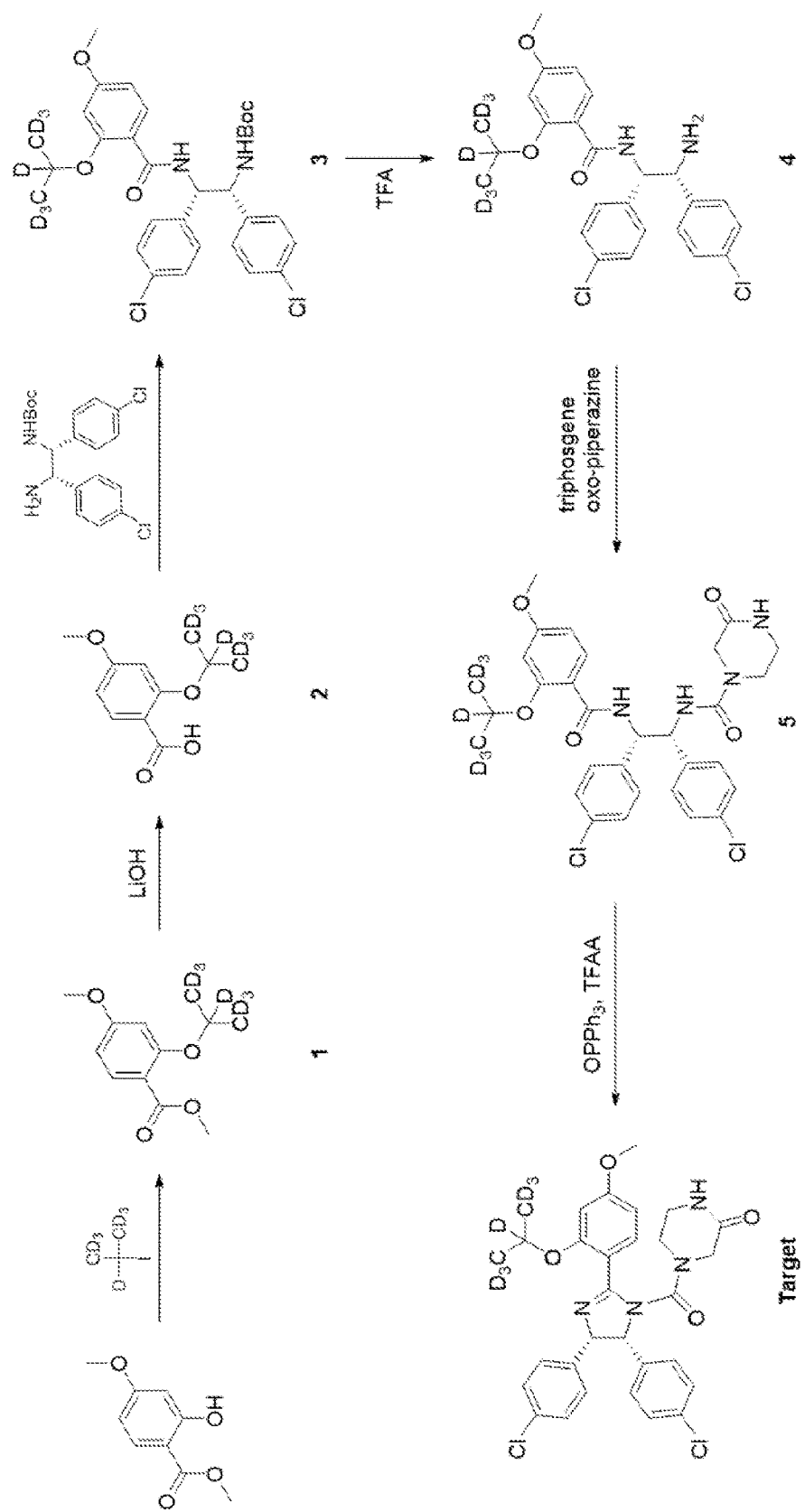

FIG. 4 is a synthetic scheme used to produce Nutlin-3a labeled with deuterium. The procedure used was as follows.

Protocol 1: Synthesis of Methyl 4-methoxy-2-((propan-2-yl-d7)oxy)benzoate (1)

To a solution of methyl 2-hydroxy-4-methoxy-benzoate (199 mg, 1.09 mmol) in DMF (10 mL) were added $K_2CO_3$ (301 mg, 2.18 mmol) and [$D^7$]2-iodo-propane (195 mg, 1.10 mmol). The reaction mixture was stirred at 70° C. overnight, and then poured into water (30 mL). The resulting mixture was extracted with EtOAc (40 mL×3), and the combined organic phases were dried over anhydrous $Na_2SO_4$ and concentrated. The residue was purified by flash column chromatography on silica gel (Petroleum Ether:EtOAc=20:1) to afford Compound 1 (226 mg, yield 90%). MS (ESI) m/z=232.3 $[M+H]^+$. $^1H$ NMR (300 M, $CDCl_3$), δ 7.82 (m, 1H), 6.52-6.49 (m, 2H), 3.86 (s, 3H), 3.84 (s, 3H); $^{13}C$ NMR (100 M, CDCl$_3$), δ 166.4, 163.9, 159.8, 133.7, 113.9, 105.0, 102.1, 71.3 (m), 55.4, 51.6, 21.2 (m).

Protocol 2: Synthesis of 4-Methoxy-2-((propan-2-yl-d7)oxy)benzoic acid (2)

To a solution of Compound 1 (211 mg, 912.24 umol) in THF/H$_2$O (5 mL/5 mL) was added LiOH (66 mg, 2.75 mmol). The reaction mixture was stirred at 45° C. overnight, and then adjusted to pH 3-4. The resulting mixture was extracted with EtOAc (40 mL×3), and the combined organic phases were dried over anhydrous Na$_2$SO$_4$ and concentrated to afford Compound 2 (168 mg, 85% yield), which was used directly in the next step.

Protocol 3: Synthesis of tert-Butyl ((1R,2S)-1,2-bis(4-chlorophenyl)-2-(4-methoxy-2-((propan-2-yl-d7)oxy) benzamido)ethyl)carbamate (3)

To a solution of Compound 2 (156 mg, 715.97 umol) in DCM (15 mL) were added DIPEA (185 mg, 1.43 mmol) and HATU (518 mg, 2.15 mmol) at 0° C. This mixture was stirred at 0° C. for 30 min and then tert-butyl ((1R,2S)-2-amino-1,2-bis (4-chlorophenyl)ethyl)carbamate (273 mg, 715.97 umol) was added. The reaction mixture was stirred at r.t. overnight, and then washed with water (30 mL). The water phase was extracted with DCM (30 mL×3). The combined organic phases were dried over anhydrous Na$_2$SO$_4$ and concentrated. The residue was purified by flash column chromatography on silica gel (DCM:MeOH=50:1) to afford Compound 3 (321 mg, 77% yield). MS (ESI) m/z=602.0 [M+Na]$^+$.

Protocol 4: Synthesis of N-((1S,2R)-2-amino-1,2-bis(4-chlorophenyl)ethyl)-4-methoxy-2-((propan-2-yl-d7)oxy)benzamide (4)

To a solution of Compound 3 (385 mg, 699.34 umol) in DCM (7 mL) was added TFA (3 mL) at r.t. The reaction mixture was stirred at r.t. for 2 hr., and then poured into aq. Na$_2$CO$_3$ (20 mL). The resulting mixture was extracted with DCM (30 mL×3). The combined organic phases were dried over anhydrous Na$_2$SO$_4$ and concentrated to afford Compound 4 (301 mg, 96% yield), which was used in the next step without further purification.

Protocol 5: Synthesis of N-((1R,2S)-1,2-bis(4-chlorophenyl)-2-(4-methoxy-2-((propan-2-yl-d7)oxy)benz-amido)ethyl)-3-oxopiperazine-1-carboxamide (5)

To a solution of Compound 4 (315 mg, 706.29 umol) in DCM (10 mL) was added CDI (153 mg, 1.06 mmol). The mixture was stirred at r.t. for 1.5 hr. and then piperazin-2-one (85 mg, 848.98 umol) was added. The reaction mixture was stirred overnight, concentrated and then directly purified by prep-TLC to afford Compound 5 (318 mg, 74% yield). MS (ESI) m/z=606.4 [M+H]$^+$. $^1$H NMR (400M, CDCl$_3$): δ 8.39 (m, 1H), 8.26 (m, 1H), 7.28 (m, 2H), 7.19 (m, 2H), 6.96 (m, 2H), 6.93 (m, 2H), 6.62 (m, 2H), 5.76 (m, 1H), 5.09 (m, 1H), 4.17 (m, 2H), 3.86 (s, 3H), 3.74 (m, 1H), 3.62 (m, 1H), 3.42 (m, 2H).

Protocol 6: Synthesis of [D$^7$]Nutlin-3a

To a solution of triphenylphosphine oxide (130 mg, 496.18 umol) in DCM (10 mL) was added Tf$_2$O (140 mg, 496.45 umol) at 0° C. The mixture was stirred at 0° C. for 30 min and then Compound 5 (301 mg, 496.25 umol) was added. The reaction mixture was stirred at r.t. overnight, and then poured into water (15 mL). The resulting mixture was extracted with DCM (20 mL×3), and the combined organic phases were dried over Na$_2$SO$_4$ and concentrated. The residue was purified by prep-HPLC to afford [D$^7$]Nutlin-3a (151 mg, 52% yield). MS (ESI) m/z=589.9 [M+H]$^+$. $^1$H NMR (400M, MeOH-d$_4$): δ 7.59 (m, 1H), 7.14 (m, 2H), 7.05 (m, 4H), 6.94 (m, 2H), 6.67 (m, 2H), 5.76 (m, 1H), 5.57 (m, 1H), 3.87 (s, 3H), 3.77 (m, 2H), 3.38 (m, 2H), 2.92 (m, 2H). $[α]_D$=−135.6° (c=0.1, CHCl$_3$) while $[α]_D$=−140° (c=0.18, CHCl$_3$) for Nutlin-3a.

Example C: Measuring MDM2 Inhibition

MDM2 (mouse double minute 2 homolog, also known as E3 ubiquitin-protein ligase) is a negative regulator of the p53 tumor suppressor. Inhibiting MDM2 promotes p53 activity, thereby conferring senolytic activity. The ability of compounds to act as agonists for MDM2 can be measured indirectly in cells by monitoring the effect on p53.

A p53 luciferase reporter RKO stable cell line can be obtained from Signosis Inc., Santa Clara Calif. In the p53 luciferase cell line, luciferase activity is specifically associated with the activity of p53. The cell line was established by transfection of a p53 luciferase reporter vector along with a G418 expression vector, followed by G418 selection.

The assay is conducted as follows. Cells from the reporter cell line are treated for 24 h with the candidate compound. Media is then removed, the cells are washed with PBS, and 20 µL of lysis buffer is added to each well. Cells are shaken for 10 s using a plate reader agitator. Luciferase buffer is prepared and added to the wells. p53 activity is then read using a Victor™ multilabel plate reader (PerkinElmer, San Jose Calif.).

Example D: Measuring Senolytic Activity

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% O$_2$, 10% CO$_2$, and ~95% humidity. The cells are divided into three groups: irradiated cells (cultured for 14 days after irradiation prior to use), proliferating normal cells (cultured at low density for one day prior to use), and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 µL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Mass.) and cultured for 5 min until the cells have rounded up and begin to detach from the plate. Cells are dispersed, counted, and prepared in medium at a concentration of 50,000 cells per mL. 100 µL of the cells is plated in each well of a 96-well plate. Medium is changed on day 13.

On day 13, the proliferating healthy cell population is prepared as follows. Healthy IMR90 cells are washed, combined with 3 mL of TrypLE and cultured for 5 minutes until the cells have rounded up and begin to detach from the plate. Cells are dispersed, counted, and prepared in medium at a concentration of 25,000 cells per mL. 100 μL of the cells is plated in each well of a 96-well plate.

On day 14, test Bcl-2 inhibitors or MDM2 inhibitors are combined with the cells as follows. A DMSO dilution series of each test compound is prepared at 200 times the final desired concentration in a 96-well PCR plate. Immediately before use, the DMSO stocks are diluted 1:200 into pre-warmed complete medium. Medium is aspirated from the cells in each well, and 100 μL/well of the compound containing medium is added.

To test senolytic activity of cis-imidazolines prepared according to this invention, the compound is cultured with the cells for 6 days, replacing the culture medium with fresh medium and the same compound concentration on day 17. Bcl-2 inhibitors like 001967 are cultured with the cells for 3 days.

The assay system uses the properties of a thermostable luciferase to enable reaction conditions that generate a stable luminescent signal while simultaneously inhibiting endogenous ATPase released during cell lysis. At the end of the culture period, 100 μL of CellTiter-Glo® reagent (Promega Corp., Madison, Wis.) is added to each of the wells. The cell plates are placed for 30 seconds on an orbital shaker, and luminescence is measured.

Likewise, the ability of cis-imidazolines prepared according to this invention to kill cancer cells may be determined in a cell lysis activity in which cells are contacted with the test compound. The effect on cancer cells is compared with the effect on non-cancer cells of the same tissue origin.

INCORPORATION BY REFERENCE

Exemplary procedures provided in this disclosure do not limit the claimed invention unless explicitly stated. To the extent compatible, the synthesis methods of this invention may be used to produce any of the structures disclosed in U.S. Pat. Nos. 6,734,302; 6,617,346; and 7,705,007 and in pre-grant publications US 2005/0282803 A1; US 2007/0129416 A1; and US 2013/0225603 A1.

All publications, patents, and patent applications referred to in this specification are hereby incorporated herein by reference in their entirety for all purposes to the same extent as if each individual publication, patent, or patent application was specifically and individually indicated to be incorporated by reference.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed.

What is claimed is:

1. A method for chemically synthesizing a cis-imidazoline with an enantiomeric excess (ee) of at least 90%, the method comprising:
   (a) obtaining a racemic mixture of a precursor according to Formula (A);

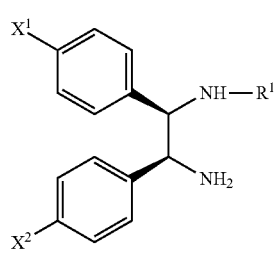

(A)

wherein $X^1$ and $X^2$ are both halogen, the first nitrogen is bonded to $R^1$ which is a first substituent having the formula —C(=O)—$R^2$ where $R^2$ an optionally substituted carbocycle or heterocycle group, and the second nitrogen is a primary amine;
   (b) combining the racemic mixture of the precursor with a chiral aromatic acid according to Formula (B):

HOOC—CH(OH)—$R^3$ (B)

wherein $R^3$ is an optionally substituted aryl or heteroaryl group,
   whereby a first stereoisomer of the precursor associates with the chiral aromatic acid, and a second stereoisomer of the precursor does not;
   (c) separating and recovering the first stereoisomer from the chiral aromatic acid;
   (d) selectively derivatizing the second nitrogen of the first stereoisomer with a second substituent having the formula —C(=O)—$R^4$, wherein $R^4$ is an optionally substituted carbocycle or heterocycle group; and then
   (e) performing a ring closing reaction in which the first nitrogen joins with the second nitrogen, thereby forming the cis-imidazoline with an enantiomeric excess (ee) of at least 90%.

2. A method for chemically synthesizing a cis-imidazoline with an enantiomeric excess (ee) of at least 90%, the method comprising:
   (a) obtaining a racemic mixture of a precursor according to Formula (A),

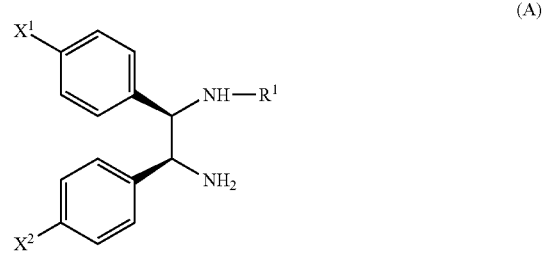

(A)

wherein $X^1$ and $X^2$ are both halogen, the first nitrogen is bonded to $R^1$ which is a nitrogen protecting group, and the second nitrogen is a primary amine;
   (b) combining the racemic mixture of the precursor with a chiral aromatic acid according to Formula (B),

HOOC—CH(OH)—$R^3$ (B)

wherein $R^3$ is an optionally substituted aryl or heteroaryl group,
   whereby a first stereoisomer of the precursor associates with the chiral aromatic acid, and a second stereoisomer of the precursor does not;
   (c) separating and recovering the first stereoisomer from the chiral aromatic acid;
   (d) selectively derivatizing the second nitrogen of the first stereoisomer with a second substituent having the formula —C(=O)—$R^4$, wherein $R^4$ is an optionally substituted carbocycle or heterocycle group;
   (e) deprotecting the first nitrogen;
   (f) selectively derivatizing the first nitrogen of the first stereoisomer with a first substituent having the formula —C(=O)—$R^2$, wherein $R^2$ is an optionally substituted carbocycle or heterocycle group, and then
   (g) performing a ring closing reaction on the first stereoisomer in which the first nitrogen joins with the second nitrogen, thereby forming the cis-imidazoline with an enantiomeric excess (ee) of at least 90%.

3. The method of claim 1 or claim 2, wherein the first or the second substituent is

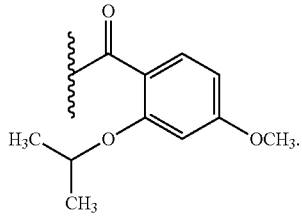

4. The method of claim 1 or claim 2, wherein the first or the second substituent is

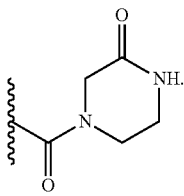 [SMILES: *C(=O)N1CCNC(=O)C1]

5. The method of claim 1 or claim 2, wherein $R^3$ is phenyl.

6. The method of claim 1 or claim 2, wherein $X^1$ and $X^2$ are both chloride.

7. The method of claim 1 or claim 2, wherein the chiral aromatic acid is D-mandelic acid or L-mandelic acid.

8. The method of claim 1 or claim 2, wherein the separating includes crystallizing molecules of the precursor with the chiral aromatic acid, and recovering the first stereoisomer from crystals formed thereby.

9. The method of claim 1 or claim 2, further comprising separating and recovering the second stereoisomer not associated with the chiral aromatic acid; and
    derivatizing and cyclizing the second stereoisomer to form a second batch of the same cis-imidazoline.

10. The method of claim 1 or claim 2, wherein the ring-closing reaction performed by combining the first stereoisomer with either triphenylphosphine oxide ($Ph_3PO$) or 2-fluoropyridine, and with either trifluoromethanesulfonic anhydride ($Tf_2O$) or trifluoroacetic anhydride (TFAA).

11. The method of claim 1 or claim 2, wherein the cis-imidazoline synthesized thereby is 4-[[(4S,5R)-4,5-bis(4-chlorophenyl)-4,5-dihydro-2-[4-methoxy-2-(1-methylethoxy)phenyl]-1H-imidazol-1-yl]carbonyl]-2-piperazinone (UBXO101).

12. The method of claim 11, wherein the cis-imidazoline prepared according to the method has an enantiomeric excess (ee) of at least 98%.

13. A method for enantiomerically enriching a cis-imidazoline precursor, comprising:
    (a) combining a racemic mixture of a precursor according to Formula (A) with a chiral aromatic acid under conditions whereby crystals selectively form between a first stereoisomer of the precursor and the chiral aromatic acid, leaving a second stereoisomer of the precursor in solution;

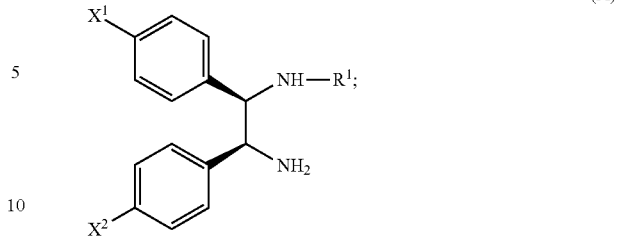

(b) separating the crystals from the solution; and
   (c) recovering the first stereoisomer from the crystals, thereby enantiomerically enriching the cis-imidazoline precursor;
   wherein $X^1$ and $X^2$ are both chloride, $R^1$ is —C(=O)—$R^2$ or an amine protecting group, and $R^2$ is an optionally substituted carbocycle or heterocycle group; and
   wherein the chiral aromatic acid is HOOC—CH(OH)—$R^3$ wherein $R^3$ is a substituted or an unsubstituted aryl or heteroaryl group.

14. The method of claim 13, wherein the chiral aromatic acid is D-mandelic acid or L-mandelic acid.

15. The method of claim 13, wherein $R^1$ is BOC or another amine protecting group.

16. The method of claim 13, wherein $R^1$ is

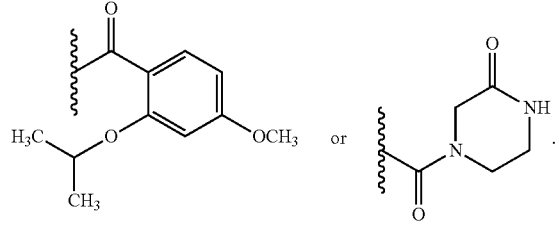 [SMILES: *C(=O)c1ccc(OC)cc1OC(C)C ; *C(=O)N1CCNC(=O)C1]

17. The method of claim 16, further comprising reacting the product of step (c) with

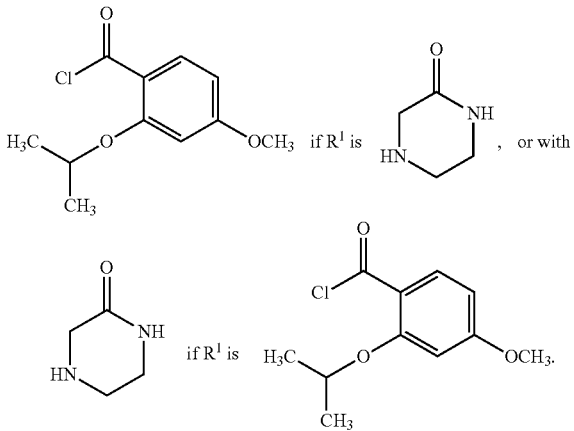

18. The method of claim 13, whereby the cis-imidazoline prepared from the product of step (c) has an enantiomeric excess (ee) of at least 90%.

* * * * *